(12) United States Patent
Hirasawa et al.

(10) Patent No.: US 8,787,647 B2
(45) Date of Patent: Jul. 22, 2014

(54) IMAGE MATCHING DEVICE AND PATIENT POSITIONING DEVICE USING THE SAME

(75) Inventors: Kosuke Hirasawa, Tokyo (JP);
Hidenobu Sakamoto, Tokyo (JP);
Ryoichi Yamakoshi, Tokyo (JP); Yasuo Kitaaki, Tokyo (JP); Shinjiro Kawato, Tokyo (JP); Haruhisa Okuda, Tokyo (JP); Hiroshi Kage, Tokyo (JP); Kazuhiko Sumi, Tokyo (JP)

(73) Assignee: Mitsubishi Electric Corporation, Tokyo (JP)

( * ) Notice: Subject to any disclaimer, the term of this patent is extended or adjusted under 35 U.S.C. 154(b) by 335 days.

(21) Appl. No.: 13/256,551

(22) PCT Filed: Jun. 7, 2010

(86) PCT No.: PCT/JP2010/003772
§ 371 (c)(1),
(2), (4) Date: Jan. 6, 2012

(87) PCT Pub. No.: WO2010/143400
PCT Pub. Date: Dec. 16, 2010

(65) Prior Publication Data
US 2012/0114208 A1    May 10, 2012

(30) Foreign Application Priority Data

Jun. 10, 2009   (JP) .................................. 2009-139230

(51) Int. Cl.
*G06K 9/00*    (2006.01)
*A61B 6/00*    (2006.01)

(52) U.S. Cl.
USPC .................................. 382/131; 378/4; 378/21

(58) Field of Classification Search
CPC .................................... G06T 1/00; A61B 1/00
USPC ......... 382/128, 129, 130, 131, 132, 133, 134, 382/209, 218, 278, 299; 378/4, 8, 21–27, 378/901; 600/407, 425; 345/419
See application file for complete search history.

(56) References Cited

U.S. PATENT DOCUMENTS 5,982,915 A * 11/1999 Doi et al. ...................... 382/130
2003/0035507 A1   2/2003 Hsu et al.
(Continued)

FOREIGN PATENT DOCUMENTS

CA    2645385    6/2009
(Continued)

OTHER PUBLICATIONS

Okuda, H., et al., "Robust Picture Matching Using Optimum Selection of Partial Templates," IEEJ Transactions on Electronics, Information and Systems, vol. 124, No. 3, pp. 629-636, (2004) (with English Abstract).
(Continued)

*Primary Examiner* — Abolfazl Tabatabai
(74) *Attorney, Agent, or Firm* — Oblon, Spivak, McClelland, Maier & Neustadt, L.L.P.

(57) ABSTRACT

An image matching device in which, in automatic positioning calculation using an ICP method, a solution is converged to an optimal solution while avoiding reaching a local solution, and a patient positioning device using this matching device. The device includes a CT image data reading unit reading first and second CT image data, a point group data generation unit generating first and second point group data in a three-dimensional space by binarization processing and edge-extraction processing on sliced images of the first and second CT image data, respectively, a point group data resolution conversion unit thinning-out point group data so as to extend a point-group-data array pitch, and an ICP calculation unit obtaining, using an ICP method, a conversion amount for the second point group data so that an error function of the first point group data and the second point group data outputted from the point group data resolution conversion unit is minimized.

10 Claims, 9 Drawing Sheets

(56) References Cited

U.S. PATENT DOCUMENTS

| | | |
|---|---|---|
| 2007/0103460 A1 | 5/2007 | Zhang et al. |
| 2007/0274582 A1 | 11/2007 | Yatziv et al. |
| 2009/0148012 A1 | 6/2009 | Altmann et al. |

FOREIGN PATENT DOCUMENTS

| | | |
|---|---|---|
| JP | 09 277184 | 10/1997 |
| JP | 2001 511570 | 8/2001 |
| JP | 2005 087727 | 4/2005 |
| JP | 2009 000369 | 1/2009 |
| JP | 2009 515493 | 4/2009 |

OTHER PUBLICATIONS

Hirooka, M., et al., "Hierarchical distributed template matching," Society of Photo-Optical Instrumentation Engineers (SPIE), Machine Vision Applications in Industrial Inspection V, vol. 3029, pp. 176-183, (1997).

International Search Report issued Aug. 10, 2010 in PCT/JP10/003772 filed Jun. 7, 2010.

Office Action issued on Jul. 13, 2012 in the corresponding Chinese Application No. 201080014788.1 (with English Translation).

Chinese Office Action issued Apr. 2, 2013, in China Patent Application No. 201080014788.1 (with English Translation).

Office Action (with English translation) issued on Jan. 29, 2014, in counterpart Chinese Appln No. 201080014788.1 (12 pages).

* cited by examiner

Fig. 3
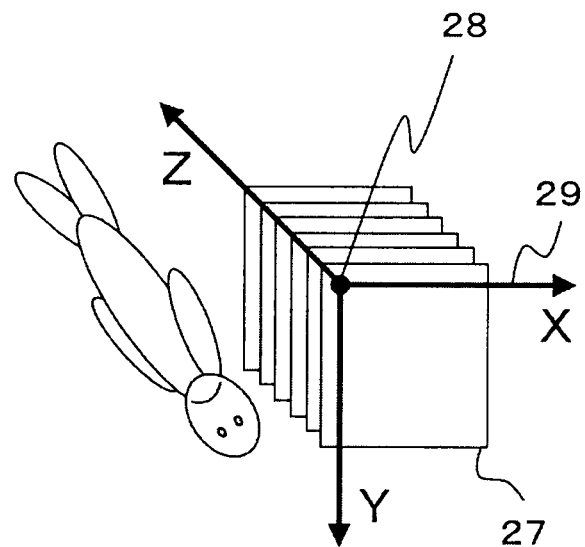
Fig. 4A
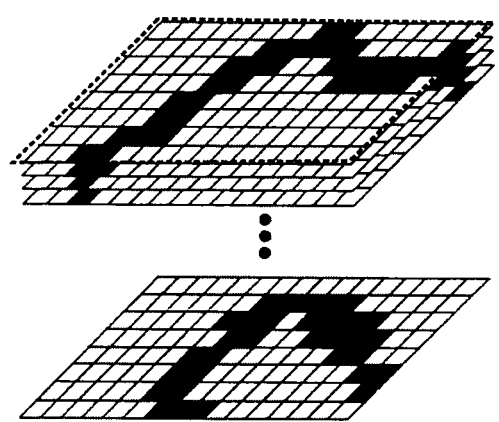
Fig. 4B
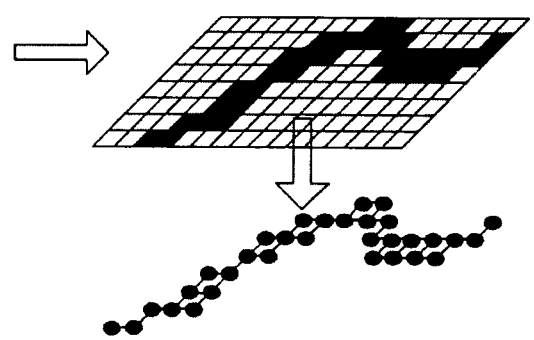
Fig. 4C

Fig. 9

| | Positioning-template previous score | Positioning-template center score | Positioning-template next score | New evaluation score |
|---|---|---|---|---|
| Treatment-plan image 1 | P1 | C1 | N1 | |
| Treatment-plan image 2 | P2 | C2 | N2 | P1+C2+N3 |
| Treatment-plan image 3 | P3 | C3 | N3 | P2+C3+N4 |
| Treatment-plan image 4 | P4 | C4 | N4 | P3+C4+N5 |
| Treatment-plan image 5 | P5 | C5 | N5 | P4+C5+N6 |
| Treatment-plan image 6 | P6 | C6 | N6 | P5+C6+N7 |
| Treatment-plan image 7 | P7 | C7 | N7 | P6+C7+N8 |
| Treatment-plan image 8 | P8 | C8 | N8 | P7+C8+N9 |
| Treatment-plan image 9 | P9 | C9 | N9 | P8+C9+N10 |
| Treatment-plan image 10 | P10 | C10 | N10 | P9+C10+N11 |
| Treatment-plan image 11 | P11 | C11 | N11 | P10+C11+N12 |
| Treatment-plan image 12 | P12 | C12 | N12 | P11+C12+N13 |
| ..... | ..... | ..... | ..... | ..... |

Fig. 10

| | Positioning-template previous score | Positioning-template center score | Positioning-template next score | New evaluation score |
|---|---|---|---|---|
| Treatment-plan image 1 | P1 | C1 | N1 | |
| Treatment-plan image 2 | P2 | C2 | N2 | |
| Treatment-plan image 3 | P3 | C3 | N3 | |
| Treatment-plan image 4 | P4 | C4 | N4 | P1+C4+N7 |
| Treatment-plan image 5 | P5 | C5 | N5 | P2+C5+N8 |
| Treatment-plan image 6 | P6 | C6 | N6 | P3+C6+N9 |
| Treatment-plan image 7 | P7 | C7 | N7 | P4+C7+N10 |
| Treatment-plan image 8 | P8 | C8 | N8 | P5+C8+N11 |
| Treatment-plan image 9 | P9 | C9 | N9 | P6+C9+N12 |
| Treatment-plan image 10 | P10 | C10 | N10 | P7+C10+N13 |
| Treatment-plan image 11 | P11 | C11 | N11 | P8+C11+N14 |
| Treatment-plan image 12 | P12 | C12 | N12 | P9+C12+N15 |
| ..... | ..... | ..... | ..... | ..... |

Fig. 11
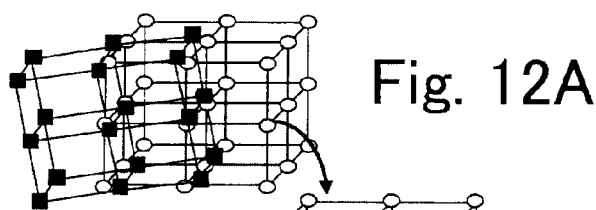
Fig. 12A
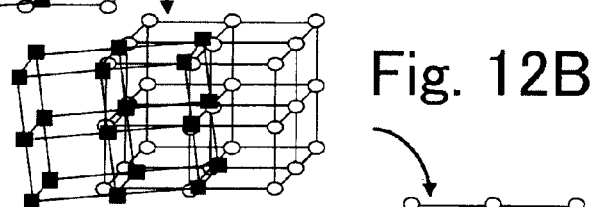
Fig. 12B
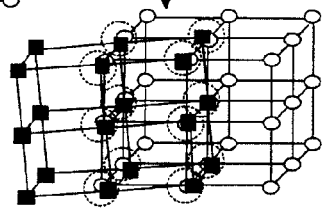
Fig. 12C

IMAGE MATCHING DEVICE AND PATIENT POSITIONING DEVICE USING THE SAME

TECHNICAL FIELD

The present invention relates to an image matching device utilizing CT (computed tomography) image data, etc., and to a patient positioning device, using the image matching device, for radiation treatment, etc.

BACKGROUND ART

As a conventional image matching method using three-dimensional point group data, an ICP (iterative closest point) method is present. The ICP method is a technique for estimating, in two sets of three-dimensional point group data (G1, G2) to be image matching targets, by sequential and iterative calculation, using the sum of distance values between corresponding points as an error function, based on least-squares estimation, suitable position/attitude conversion parameters between the three-dimensional point group data (translation amount and rotation amount), so as to minimize the error function.

In this ICP method, because all combinations of the corresponding points are calculated, explicit corresponding information between the matching data is not needed. That is, information that a point in the three-dimensional point group data G1 and a point in the three-dimensional point group data G2 are identical is not needed. Therefore, images can be matched without teaching anatomical characteristic points, etc., by a human. Image matching methods using the ICP method are applied to various fields (for example, Patent Document 1); in radiation treatment, by using as reference three-dimensional CT image data for a treatment plan obtained when the radiation treatment is planned, an image according to this data and that to three-dimensional CT image data for a positioning operation, with respect to a bone structure, obtained during treatment are matched, and the position/attitude conversion parameters for matching both the images of the data is obtained, whereby patient positioning at the time of the treatment can be achieved.

PRIOR ART DOCUMENT

Patent Document

[Patent Document 1] Japanese Laid-Open Patent Publication H09-277184 (page 2-3)

DISCLOSURE OF THE INVENTION

Problems to be Solved by the Invention

Such an image matching method using the ICP method has characteristics that an image matching calculation result depends on a structure of the three-dimensional point group data to be processed, and also depends on an initial state when the matching calculation starts. Especially, in a case in which slice thicknesses of the CT image data for the treatment plan and the CT image data for the positioning operation are small and close to their pixel spacing values, because of their higher data density, the error function becomes a shape having multiple local solutions, and the solution does not converge to the correct answer value (the optimal solution at which the error function takes the minimum value); as a result, the number of cases increases in which the solution converges to a incorrect answer value (a local solution corresponding to a local minimal value of the error function).

Regarding an image matching operation in radiation treatment, the above phenomenon is specifically explained using FIGS. 12A to 12C. Data arranged in lattice shapes with white circles at the vertices is assumed as point group data of the CT image data for the treatment plan as reference (first point group data), while data with black squares at the vertices is assumed as point group data of the CT image data for the positioning operation during the treatment as the matching target (second point group data). Additionally, in this example, the lattice spacing distances for both the point group data are assumed to be equal for simplicity.

As represented in the figure, when the densities of the first point group data and the second point group data are in higher states, in the N-th sequential and iterative calculation by the ICP method (FIG. 12B), in many cases nearest corresponding points are the same as those in the (N−1)-th calculation (FIG. 12A) increase, and in some cases the nearest corresponding points do not vary also in the (N+1)-th calculation; as a result, in such cases, the variation amount of the error function remains at a slight level.

The above state is schematically represented in FIG. 13, in which a relative positional shift between the treatment plan data group and the positioning operation data group ($\Delta x$) is taken on the horizontal axis, while a distribution of the error function (E) is on the longitudinal axis. The error function reaches the minimum when the positional shift between both the data groups does not occur ($\Delta x=0$), and has a distribution in which local minimums appear for every lattice-distance shift (d1) between both the data groups (refer to a curve E1) from the minimum state. In a case of the state of both the point group data densities being higher as described above, because the error function E1 has a local minimal value also in the case of being shifted by one lattice unit from the optimal solution ($\Delta x=0$), a problem has occurred in the ICP method that, due to the solution being determined to have converged at the local minimal value, probability of falling into a local solution (incorrect answer value, $\Delta x = \Delta x_L$) is high.

An objective of the present invention, which is made to solve the above described problem, is to provide an image matching device having higher matching accuracy, by avoiding reaching a local solution so as to surely converge to the optimal solution in an automatic positioning calculation using the ICP method, and to provide a patient positioning device using the image matching device.

Means for Solving the Problem

An image matching device and a patient positioning device using the image matching device according to the present invention each include a CT image data reading unit for reading first CT image data and second CT image data, a point group data generation unit for generating first point group data and second point group data in a three-dimensional space from sliced images of the first CT image data and the second CT image data, respectively, a point group data resolution conversion unit for thinning-out at least one of the first point group data and the second point group data so as to extend a point-group-data array pitch, and an ICP calculation unit.

Here, the ICP calculation unit is characterized in that a conversion amount for the second point group data is obtained, using an ICP method, so that an error function of the first point group data and the second point group data outputted from the point group data resolution conversion unit is minimized.

Advantageous Effect of the Invention

According to the image matching device and the patient positioning device using this image matching device of the present invention, because the point group data resolution conversion unit thins out at least one of the first point group data and the second point group data so as to extend the array pitch of the point group data, and the ICP calculation unit obtains, using the ICP method, a conversion amount for the second point group data so that the error function of the first point group data and the second point group data outputted from the point group data resolution conversion unit is minimized, as represented in FIG. 13 by the curved line (E2) after the point group data resolution has been converted, the distribution of the error function can be modified so that the pitch where the local minimal values appear is extended by the extension of the lattice pitch.

Therefore, even when the solution of the error function before the point group data resolution conversion (E1) is in a local minimal value ($\Delta x=\Delta x_L$), because, after the point group data resolution is converted (E2), that can be set not at the local minimal value, further solution search is performed by the ICP calculation unit without erroneously determining to have converged; as a result, it is possible to surely converge to the optimal solution ($\Delta x=0$).

BRIEF DESCRIPTION OF DRAWINGS

FIG. 3 is a view schematically representing the definition of a coordinate system in the image matching device according to Embodiment 1 of the present invention;

FIGS. 4A to 4C include views explaining how to create point group data from sliced images of CT image data in the image matching device according to Embodiment 1 of the present invention;

FIGS. 6A to 6C include views representing states in which point group data is divided into regions in the image matching device according to Embodiment 1 of the present invention;

FIG. 9 is representation explaining how to calculate an evaluation score when multi-layer multi templates are set using the image matching device according to Embodiment 2 of the present invention;

FIG. 10 is representation explaining how to calculate an evaluation score when multi-layer multi templates are set using the image matching device according to Embodiment 2 of the present invention;

FIG. 11 is representation explaining how to calculate an evaluation score when multi-layer multi templates are set using the image matching device according to Embodiment 2 of the present invention;

FIGS. 12A to 12C include views explaining a phenomenon in which a result of image-matching calculation using an ICP method falls into a local solution.

BEST MODE FOR CARRYING OUT THE INVENTION

Embodiment 1

Figure 1:
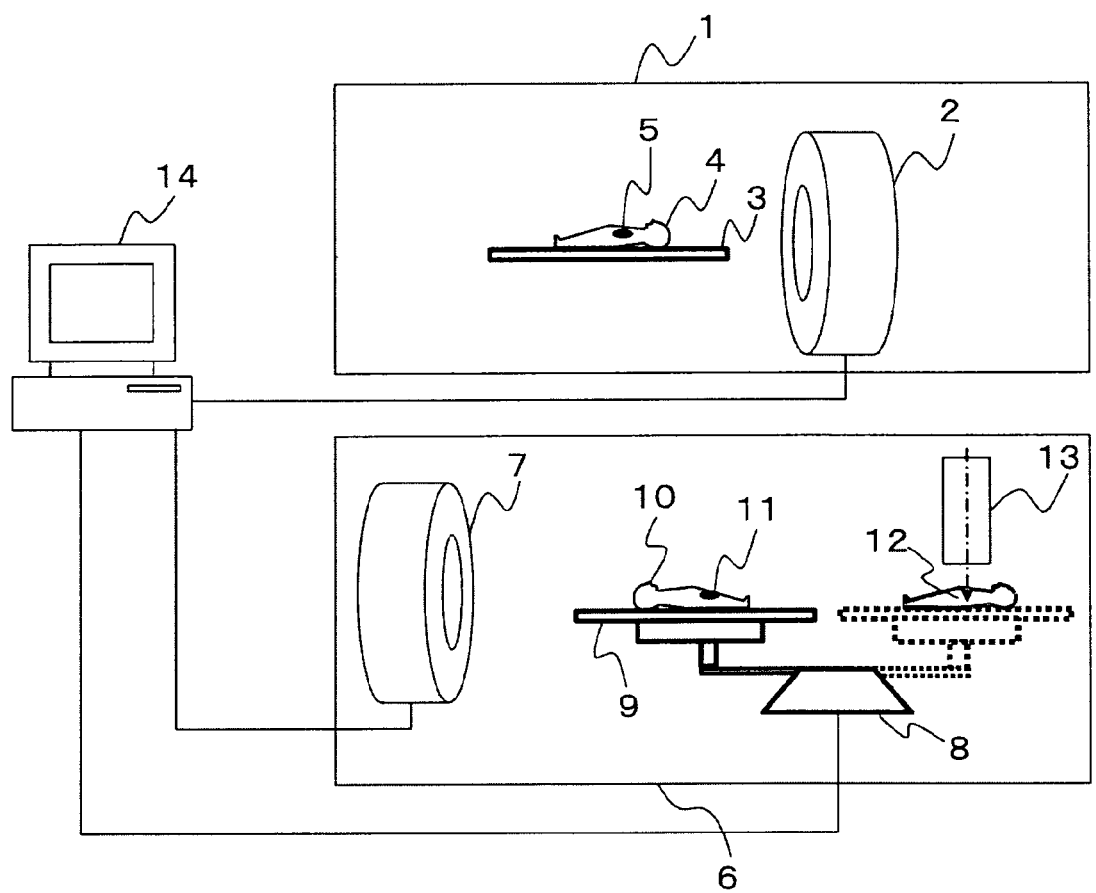
FIG. 1 is a view illustrating an overall system configuration with respect to an image matching device and a patient positioning device according to Embodiment 1 of the present invention.

FIG. 1 is a view illustrating an overall system configuration with respect to image matching, positioning, and radiation treatment using CT image data, to which an image matching device and a patient positioning device according to Embodiment 1 of the present invention are assumed to be applied. Numeral 1 denotes a CT simulator room, for creating a treatment plan before radiation treatment, in which a CT gantry 2, and a top board 3 of a bed for taking CT images are included, and, by laying a patient 4 on the top board 3, CT image data for a treatment plan is taken so that an affected part 5 is included.

On the other hand, numeral 6 denotes a treatment room for the radiation treatment, in which a CT gantry 7, a rotatable treatment table 8, and a top board 9 provided over the rotatable treatment table 8 are included, and, by laying a patient 10 on the top board 9, CT image data for a positioning operation is taken so as to include an affected part 11 for the treatment.

Here, the positioning operation means that positions of the patient 10 and the affected part 11 during the treatment are determined from the CT image data for the treatment plan, a body-position correction amount is calculated so as to match the treatment plan, and then the position of the affected part 11 during the treatment is aligned so as to be at a beam irradiation center 12 during the radiation treatment. The position alignment is realized by drive-controlling the rotatable treatment table 8, with the patient 10 lying on the top board 9, to move the position of the top board 9. Regarding the rotatable treatment table 8, translation-and-rotation six-degree-of-freedom (6DOF) drive compensation can be performed, and by rotating by 180 degrees the top board 9 of the rotatable treatment table 8, the top board can also be moved from a CT image taking position (indicated by solid lines in FIG. 1) to a treatment position where an irradiation head 13 is arranged (indicated by broken lines in FIG. 1). Here, in FIG. 1, an example is represented in which the CT image taking position and the treatment position are in 180 degree opposed-position relationship; however, the alignment is not limited that, but their positional relationship may be at other angles such as 90 degrees.

Here, the CT image data for the treatment plan and the CT image data for the positioning operation are transmitted to a positioning computer 14. Both the image matching device and the patient positioning device according to the present invention relate to computer software included in this positioning computer, in which the image matching device calculates the body-position correction amounts (translation amounts and rotation amounts), while the patient positioning device includes the image matching device and also has a function for calculating parameters for controlling, based on the body-position correction amounts, the driving axes of the treatment table.

In the conventional positioning operation in the radiation treatment, a positional shift amount has been calculated by matching a DRR (digitally reconstructed radiography) image generated from the CT image data for the treatment plan and an X-ray perspective image taken in the treatment room during the treatment. Because, in the X-ray perspective image, an image of an affected part as a soft tissue cannot be clearly taken, position alignment using a bone is a fundamental method. The CT positioning operation described in this embodiment has characteristics that, because the CT gantry 7 is placed together in the treatment room 6 and the position alignment is performed using the CT image data just before the treatment and the CT image data for the treatment plan, the affected part can be directly visualized, and the position alignment can be performed at the affected part.

Figure 2:
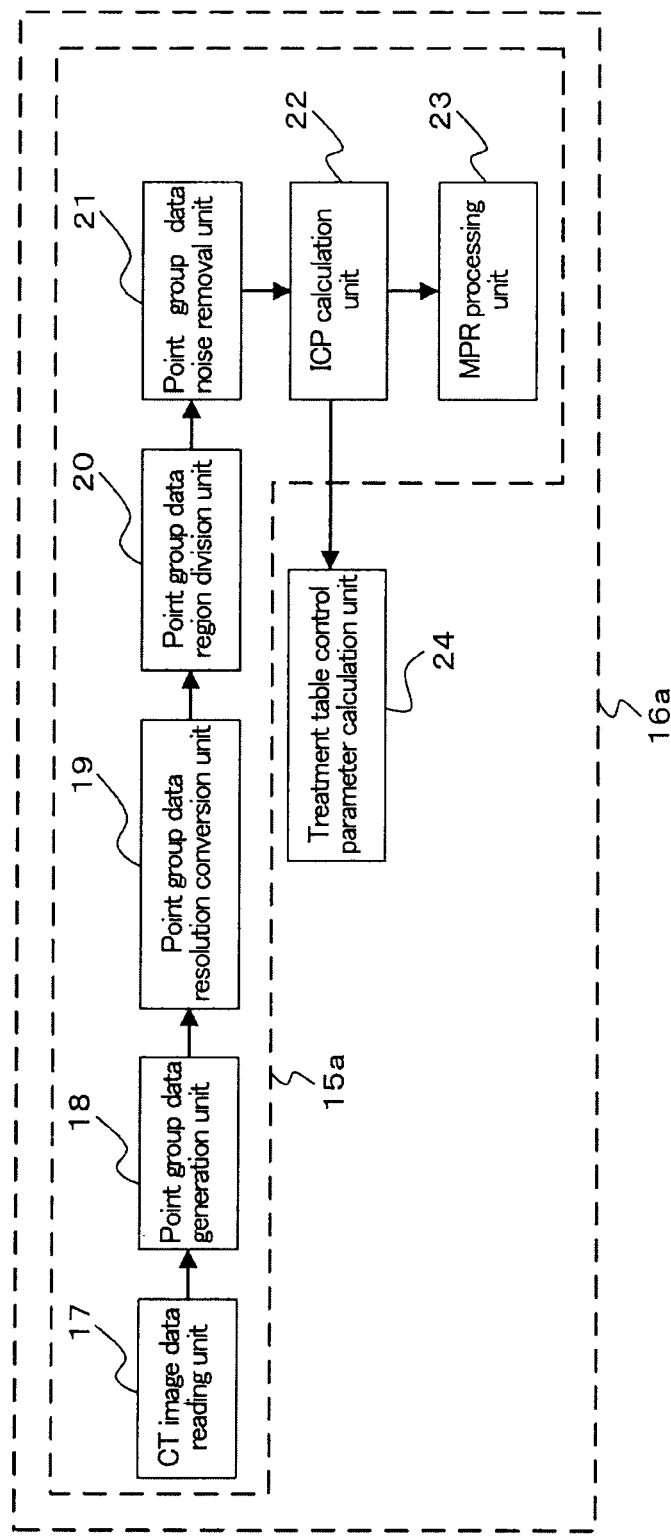
FIG. 2 is a diagram representing relationships among data processing units configuring the image matching device and the patient positioning device according to Embodiment 1 of the present invention.

Next, calculation procedures of the body-position correction amounts in the image matching device and the patient positioning device according to this embodiment will be explained. FIG. 2 is a configuration diagram illustrating relationships among data processing units constituting the image matching device and the patient positioning device, in which an image matching device 15a is configured with a CT image data reading unit 17, a point group data generation unit 18, a point group data resolution conversion unit 19, a point group data region division unit 20, a point group data noise removal unit 21, an ICP calculation unit 22, and an MPR processing unit 23, and a device in which a treatment table control parameter calculation unit 24 is added to the image matching device is a patient positioning device 16a.

In the CT image data reading unit 17, CT image data for the treatment plan (first CT image data) and that for the positioning operation (second CT image data) are read. The CT image data is constituted of sliced images in DICOM (digital imaging and communication in medicine) format; however, the format is not especially limited thereto.

In the point group data generation unit 18, point group data based on the CT image data for the treatment plan (first point group data) and that based on the CT image data for the positioning operation (second point group data) are generated from the sliced images of the CT image data for the treatment plan and the CT image data for the positioning operation. The point group data here indicates point data aggregation in a three-dimensional space, in which, regarding the three-dimensional space, for example, as illustrated in FIG. 3, among sliced images 27, a coordinate system 29 is set on a sliced image including a CT origin 28 corresponding to a reference point when the CT images are taken, and a right-handed coordinate system may be configured in such a way that the X-axis is in a horizontal direction in the sliced image plane, the Y-axis is in a direction perpendicular to the X-axis in the sliced image plane, and the Z-axis is in a direction perpendicular to the sliced image plane. The scale of the coordinate system can be determined by a pixel spacing value or a slice pitch that are tag information of the DICOM format file.

Figure 5:
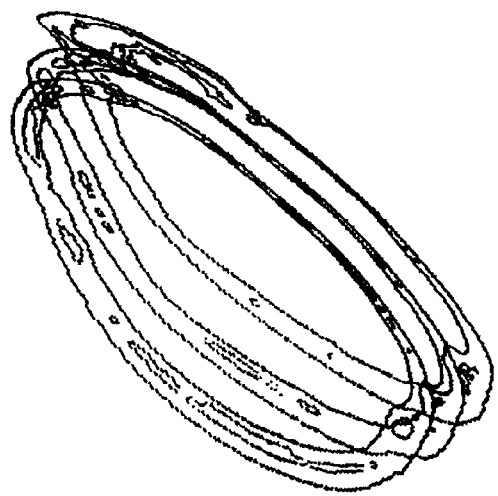
FIG. 5 is a view illustrating an example in which point group data of bone outline images is created in the image matching device according to Embodiment 1 of the present invention.

Specific point-group-data generation processing is described. By binarizing the sliced images by threshold processing, a bone region is extracted. Sequentially, edge extraction processing is performed on the binarized image, thinning processing is performed, and thus a bone outline image is obtained. In the edge extraction processing and the thinning processing, the Canny method or the like can be used; however, the method is not limited thereto, but other image matching techniques that can give a similar function may be applied. Point group data is generated from data on the outline in the bone outline image. The point group data is a set of points having three-dimensional coordinates (x, y, z). FIGS. 4A to 4C are schematic representation of an example in which, for a sliced image among sliced images (FIG. 4A), a bone outline image is created (FIG. 4B), and point group data (FIG. 4C) is generated from data on the outline in the bone outline image. FIG. 5 is schematic representation of an example in which point group data is created from three bone outline images.

In the point group data resolution conversion unit 19, by thinning-out at least one of the first point group data for the treatment plan and the second point group data for the positioning operation so as to extend the array pitch of the point group data, the data amount is adjusted. Providing that the resolution when the point group data is generated by the point group data generation unit 18 is defined to be 1/1, the resolution in the case of thinning out one out of every two points therefrom can be defined to be 1/2, three out of every four points to be 1/4, and seven out of every eight points to be 1/8. Also, in a case of the resolution being smaller than 1/8, it is assumed to be similarly defined. As for the thinning-out order, the thinning-out operation is performed in the identical sliced image plane by the appearance order of the points when raster scanning is performed, when processing over slices, the thinning direction may be determined to be, for example, from the head top to the head tail. However, the order has no meaning; therefore, processing of random thinning-out from the entire point group data may be performed. Moreover, the denominator with respect to the thinning-out operation is not needed to be a power of two.

In the point group data region division unit 20, each of the first point group data and the second point group data generated in the point group data generation unit 18 and the point group data resolution conversion unit 19 is divided into regions. For example, a system may be introduced in which, by setting the barycentric position of the point group data as the origin, dual division can be performed for each of the x-axis, y-axis, and z-axis. For example, if the division is performed only for the x-axis, it means the data is divided into two sets, and if the dual division is performed for all the axes (x-axis, y-axis, and z-axis), it means the data is divided into eight sets in all. In this case, it is not necessary to actually divide data to store as different variables or files, but a system may be introduced in which a region to which each point of the point group data belongs is kept as an attribute value thereof.

Figure 6A:
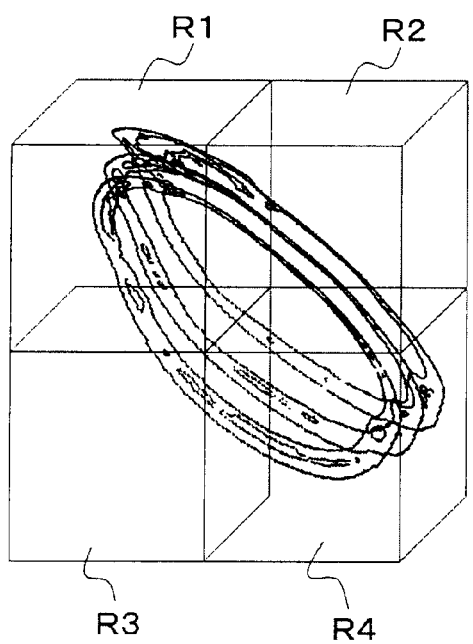
Figure 6B:
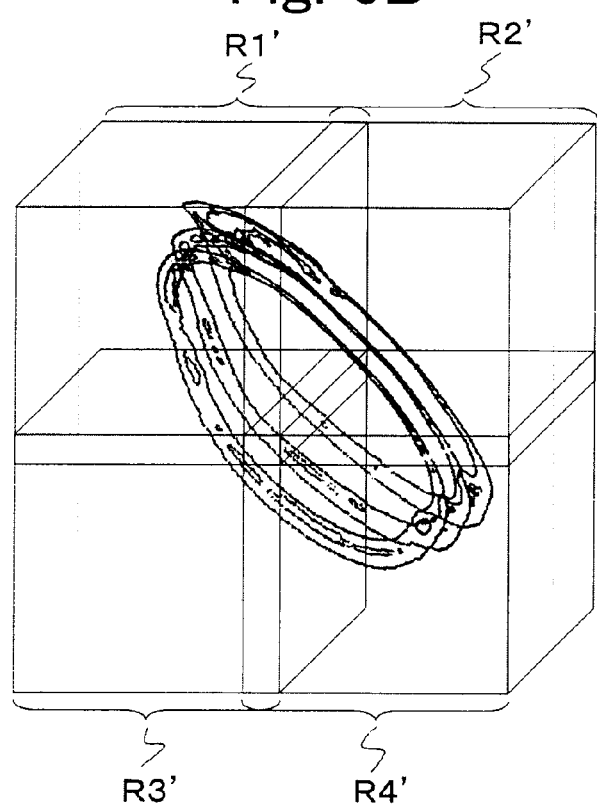

An example is illustrated in FIGS. 6A and 6B, in which the second point group data for the positioning operation and the first point group data for the treatment plan are divided into four regions from R1 to R4 (FIG. 6A) and four regions from R1' to R4' (FIG. 6B), respectively. Both the first point group data and the second point group data have to be similarly divided into regions, where the divided regions of the first point group data includes the respective divided regions of the second point group data, and, considering the positional shift between both the point group data, by setting margin regions, the divided regions of the first point group data have to be larger than those of the second point group data.

In contrast, in a case of the first point group data for the treatment plan being matched with the second point group data for the positioning operation, the divided regions of the second point group data are needed to include those of the first point group data by providing margin regions in the divided regions of the second point group data to make the divided regions of the second point group data larger than those of the first point group data.

In the point group data noise removal unit 21, if the top board 3 or 9, or a part of clothes worn by the patient 4 or 10, etc., other than bone regions is imaged in the first point group data and the second point group data generated in the point group data generation unit 18 and the point group data resolution conversion unit 19, its corresponding part of the data is removed. Because physical positions of the top boards 3 and 9 are previously known, and regarding the top boards 3 and 9 and the clothes worn by the patient 4 and 10, their CT values range around values different from that of the bone, they can be determined to be data other than those of target regions for image-matching; therefore, by utilizing the coordinate information and the CT values, these can be easily removed.

In the ICP calculation unit 22, using the first point group data for the treatment plan and the second point group data for the positioning operation, generated through the point group data generation unit 18, the point group data resolution conversion unit 19, the point group data region division unit 20, and the point group data noise removal unit 21, the conversion amount (body-position correction amount) for the second point group data is obtained, by calculating what conversion is performed on positions and attitudes of the second point group data, to be able to approximate the first point group data most, that is, so that an error function between them is minimized.

Specific processing steps are represented as follows. As an index representing correspondence between two points in the three-dimensional space, the distance between the two points is used. Here, the distance between the two points $x_1$ and $x_2$ in the three-dimensional space is expressed as $d(x_1, x_2)$.

Figure 7:
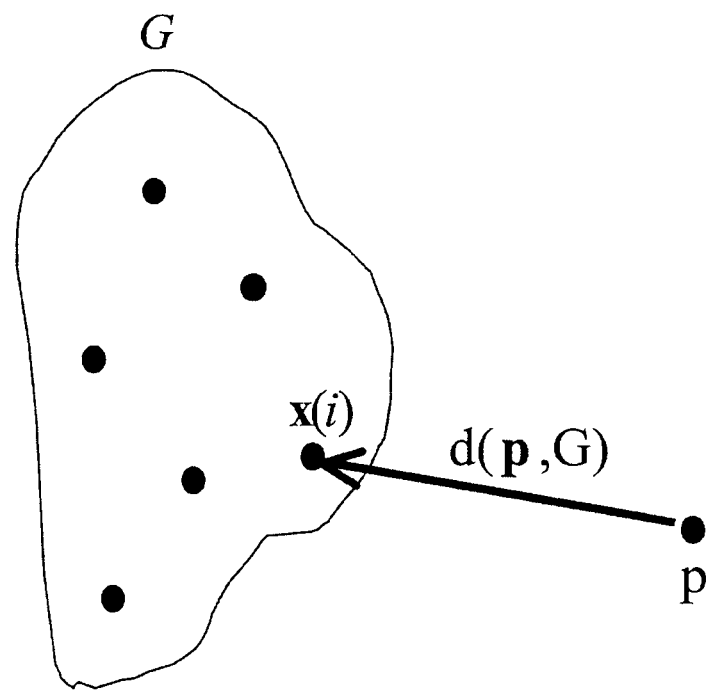
FIG. 7 is a schematic view illustrating the definition of a distance between an arbitrary point and a point group, in the image matching device according to Embodiment 1 of the present invention.

Moreover, assuming that NR point data ($x(i)$: $i=1, 2, \ldots,$ NR) is included in a point group G, the distance between an arbitrary point p and the point group G is defined, as expressed by Equation 1, to be the distance between a point nearest to the point p among points included in the point group G, and the point p (refer to FIG. 7).

$$d(p, Z) = \min_i (d(p, x(i))) \quad \text{[Equation 1]}$$

Here, it is assumed that a point group composed of $N_{ref}$ point data ($x_{ref}(i)$: $i=1, 2, \ldots, N_{ref}$) included in the first point group data (for the treatment plan) is $G_{ref}$, while that composed of $N_{test}$ point data ($x_{test}(j)$: $j=1, 2, \ldots, N_{test}$) included in the second point group data (for the positioning operation) is $G_{test}$.

First, as Step 1, the distance between the point $x_{ref}(i)$ included in the first point group data $G_{ref}$ and the second point group data $G_{test}$ is obtained, and by setting the point $x_{test}(j)$ at that time to be a corresponding point $x'_{test}(i)$ to the $x_{ref}(i)$, corresponding relationships between the first point group data $G_{ref}$ and the second point group data $G_{test}$ are obtained.

$$d(x_{ref}(i), G_{test}) = \quad \text{[Equation 2]}$$
$$\min_{1 \leq j \leq N_{test}} (d(x_{ref}(i), x_{test}(j))) \Rightarrow x_{ref}(i) \to x_{test}(j)(x'_{test}(i))$$

Next, as Step 2, a conversion amount (rotation amount R, translation amount t) from the second point group data $G_{test}$ to the first point group data $G_{ref}$ is obtained. Here, the rotation amount R is expressed in a 3×3 matrix, while the translation amount t is expressed in a 3×1 matrix. Vector difference values each between a point obtained by converting a point $x'_{test}(i)$ in the second point group data $G_{test}$ by the rotation amount R and the translation amount t, and the point $x_{ref}(i)$, which belong to the first point group data $G_{ref}$, corresponding to the point $x'_{test}(i)$ are obtained, and their square sum is defined as an error $e^2(R, t)$ (Equation 3). A rotation amount R* and a translation amount t*, when the value of $e^2(R, t)$ is the minimum, is defined to be a conversion amount at that time (Equation 4).

$$e^2(R, t) = \sum_i \|x_{ref}(i) - Rx'_{test}(i) - t\|^2 \quad \text{[Equation 3]}$$

$$(R^*, t^*) = \arg\min_{R,t} e^2(R, t) \quad \text{[Equation 4]}$$

Next, as Step 3, according to the conversion amount obtained by Step 1 and Step 2, each of the points that belong to the second point group data $G_{test}$ is converted; where k is defined as an iterative-calculation index in the ICP method.

$$x_{test\_k+1}(i) = R^*_k x_{test\_k}(i) + t^*_k \quad \text{[Equation 5]}$$

Iterative calculation is performed in Step 1 through Step 3. When a variation amount of an error in Step 2 by the iterative calculation reaches a predetermined threshold value or lower, the calculation is completed. Thus, values (rotation amount Rs*, translation amount ts*) obtained by synthesizing all the conversion amounts (rotation amount R*, translation amount t*) obtained through the iterative calculation is to be a conversion amount from the second point group data $G_{test}$ to the first point group data $G_{ref}$.

As described above, a corresponding operation is performed from each of the points included in the second point group data (for the positioning operation) to the nearest point in the first point group data (for the treatment plan), and thus the conversion amount (rotation amount R*, translation amount t*) that minimize an error function $e^2(R, t)$ defined by the sum of the distances between the positioning data group and the treatment plan data group can be obtained by sequential and iterative calculation.

Next, the MPR processing unit 23 is explained. The MPR (multi planar reconstruction/reformat) processing is a method of creating one volume data set by stacking a number of sliced images of the CT image data, to generate arbitrary sectional images on the basis of the data, which is called as "oblique processing", or also as "double oblique processing". Therefore, by using this processing, even if the data is image data which is not actually taken, such as a sagittal sectional image or a coronal sectional image, such data can be created by interpolation-processing image data of an axial section which is actually taken, for reconstruction.

As an interpolation algorithm, non-linear interpolation algorithms such as tricubic interpolation one, which is extended trilinear interpolation (TLI) one, can be also used other than linear interpolation algorithms such as the TLI. By setting a point (X, Y, Z) included in an initial section such as an axial section, a sagittal section, and a coronal section, and by setting a rotation amount (A, B, C) around each of the coordinate axes when orthogonal coordinate axes are defined using the point as a rotation center and the initial section as a reference, an oblique section is determined, and image data in the oblique section can be calculated.

If the CT image data for the treatment plan (the first CT image data) and that for the positioning operation (the second CT image data) are evaluated in respective MPR sections in which oblique-section creation parameters (X, Y, Z, A, B, C) are the same, the images do not match with each other before the automatic positioning operation, that is, they are shifted from each other.

Then, in the results from the ICP calculation unit 22 (rotation amount Rs*, translation amount ts*), by defining each component of the translation amount ts* as ($\Delta X, \Delta Y, \Delta Z$), and replacing the rotation amount Rs* with that (ΔA, ΔB, ΔC) around each axis of the X-axis, Y-axis, and Z-axis, the MPR section is created using oblique-section creation parameters (X-ΔX, Y-ΔY, Z-ΔZ, A-ΔA, B-ΔB, C-ΔC) from the CT image data for the positioning operation; thereby, an image in which the CT image data for the positioning operation is converted to approximate the treatment plan CT image data can be created. Additionally, by using the MPR section having been initially created, and by using data obtained by rotating and translating the CT image data for the positioning operation (the second CT image data) by (ΔX, ΔY, ΔZ, ΔA, ΔB, ΔC), an image close to the CT image data for the treatment plan (the first CT image data) can also be obtained, and the matching can be performed.

According to this operation, confirmation can be achieved whether bone structures of the CT image data for the positioning operation and that for the treatment plan match with each other, and determination can be performed whether the positioning result is appropriate or not.

As initial sections for checking the image, orthogonal three sections constituted of the axial section, the sagittal section, and the coronal section, etc., may be adopted, sections tilting from the axial section, the sagittal section, and the coronal section may be adopted, or combinations of those may also be adopted. Moreover, a system may be configured in which a treatment-plan image and a positioning-operation image are differentially displayed or overlappingly displayed, and the difference therebetween is checked.

Inversely, by inverting the plus/minus sign of the result obtained by the ICP calculation unit 22, the MPR section is created using oblique-section creation parameters (X+ΔX, Y+ΔY, Z+ΔZ, A+ΔA, B+ΔB, C+ΔC) from the CT image data for the treatment plan; thereby, an image in which the CT image data for the treatment plan (the first CT image data) is converted to approximate that for the positioning operation (the second CT image data) can also be created.

In the treatment table control parameter calculation unit 24, the output values from the ICP calculation unit 22 (total 6DOF consisting of translation three-axes [ΔX, ΔY, ΔZ] and rotation three-axes [ΔA, ΔB, ΔC]) are converted into parameters for controlling respective axes of the treatment table, to control the treatment table. According to this operation, the body-position correction amount is calculated so as to match the treatment plan, and thus the alignment can be performed so that the affected part 11 during the treatment is placed at the beam irradiation center 12 of the radiation treatment.

Figure 13:
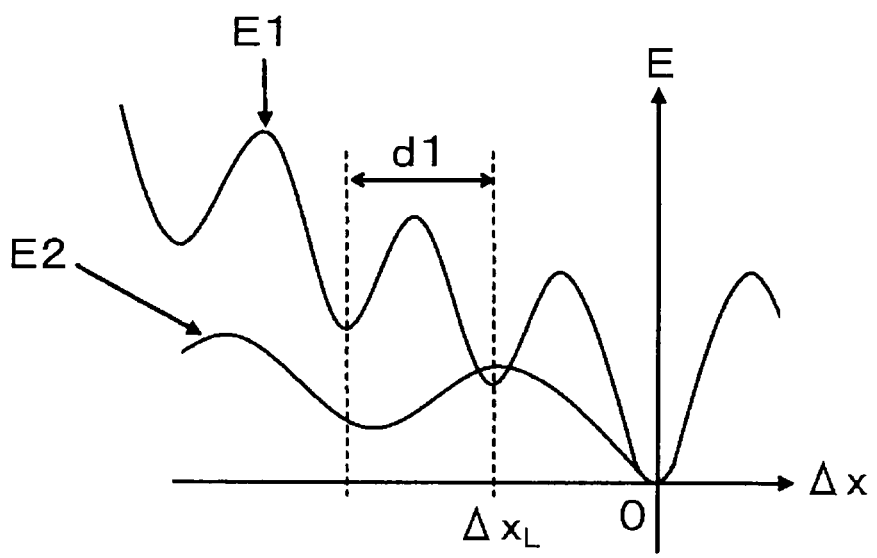
FIG. 13 is a graph explaining the difference between error-function distributions before and after point-group-data resolution conversion processing.

As described above, according to the image matching device 15a and the patient positioning device 16a of this embodiment, the point group data resolution conversion unit 19 thins out at least one of the first point group data and the second point group data so as to extend the array pitch of the point group data, and the ICP calculation unit 22 obtains a conversion amount for the second point group data using the ICP method so that the error function between the first and the second point group data outputted from the point group data resolution conversion unit 19 is minimized; therefore, as represented in FIG. 13 by a curved line (E2) after the point group data resolution has been converted, distribution of the error function can be modified so that a pitch where the local minimal values appear is extended by the extension of the lattice pitch.

Therefore, because even if an error function (E1) before the point group data resolution conversion is at a local minimal value ($\Delta x = \Delta x_L$), the error function (E2) after the conversion can be set not to take a local minimal value, further solution search is performed by the ICP calculation unit 22 without erroneously determining that the solution has converged, and consequently it becomes possible to surely converge to the optimal solution ($\Delta x = 0$).

The image matching device 15a and the patient positioning device 16a according to this embodiment includes the region division unit 20 for dividing the first point group data into a plurality of regions, and for dividing the second point group data into a plurality of regions corresponding thereto, where the ICP calculation unit 22 calculates only between each region of the first point group data and that of the second point group data corresponding thereto; therefore, a calculation amount when calculating the nearest corresponding points can be reduced compared with a case of calculating all combinations of corresponding points for the entire region before dividing, so that high-speed processing can be realized. As for the calculation amount, regarding the first point group data for the treatment plan and the second point group data for the positioning operation, if each data region is divided into N regions, the total calculation amount can be reduced approximately to 1/N (exactly, because of the presence of margin regions, a value slightly larger than 1/N is actually obtained).

The image matching device 15a and the patient positioning device 16a according to this embodiment further includes the point group data noise removal unit 21 for removing, from at least one of the first point group data and the second point group data, noise data in the part other than those of target regions for image-matching, and the ICP calculation unit 22 calculates using the first point group data and the second point group data from which the noise data is removed; therefore, erroneous correspondences between the first point group data for the treatment plan and the second point group data for the positioning operation are reduced, and an effect is resultantly obtained that the most suitable resolution is introduced without falling into a local solution by the iterative calculation in the ICP calculation unit 22.

Here, in the above description, an example has been explained in which, in the point group data generation unit 18, a bone region is extracted, the edge extraction processing is performed on the binarized image, the thinning processing is performed to obtain a bone outline image, and using this image the image matching is performed; however, instead of the bone region, the image matching can also be performed on an affected part or an organ to which the radiation treatment is to be performed. In this case, the extraction may be performed by binarizing the affected part or the organ using a specified CT value. Because the subsequent data processing is similar to that for the bone region, the detailed description is omitted.

By performing the image matching for the affected part or the organ to which the radiation treatment is performed, and, based on the output values obtained by the ICP calculation unit 22 (total 6DOF consisting of the translation three-axes [ΔX, ΔY, ΔZ] and the rotation three-axes [ΔA, ΔB, ΔC]), and by converting the values into the parameters for controlling the axes of the treatment table by the treatment table control parameter calculation unit 24, to control the treatment table, an effect similar to the above can be obtained, and additionally, an advantage is obtained that a template matching operation explained in the following embodiment 2 can be made needless.

Embodiment 2

Figure 8:
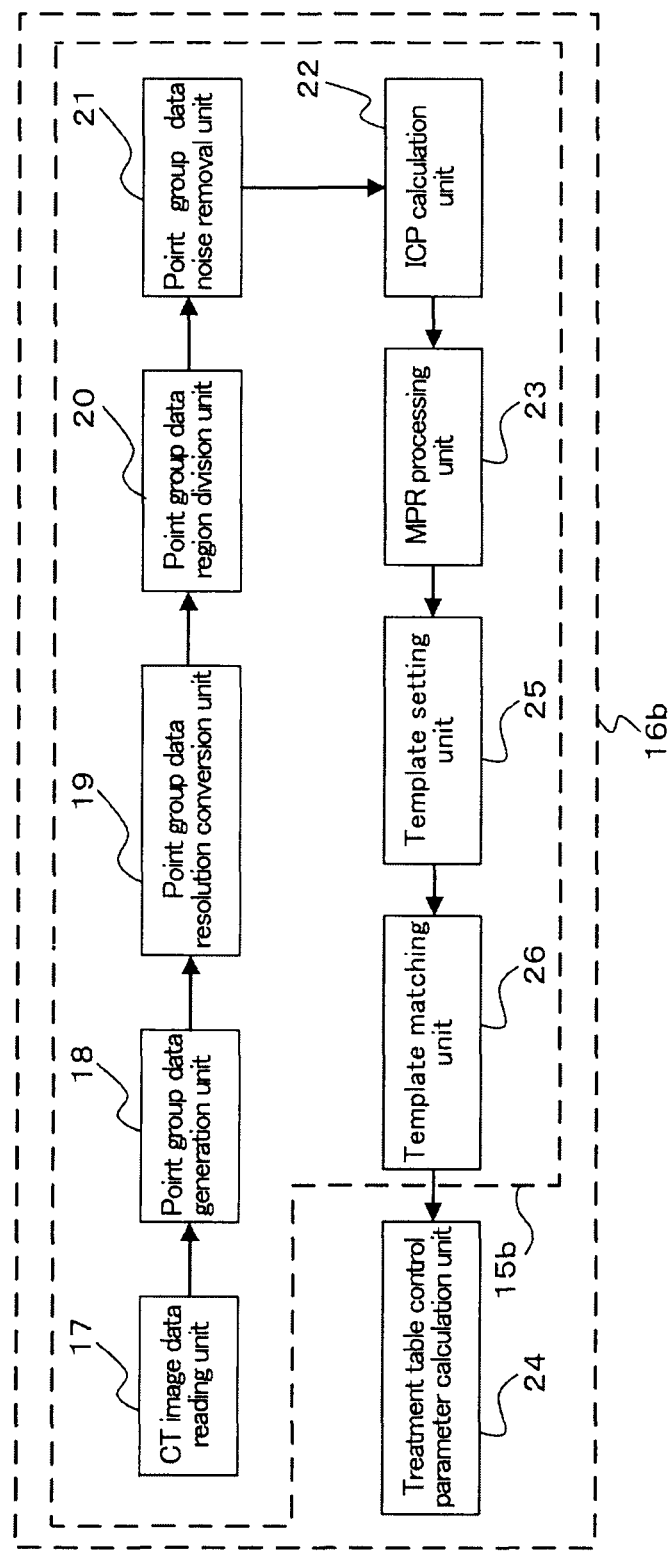
FIG. 8 is a view illustrating relationships among data processing units configuring an image matching device and a patient positioning device according to Embodiment 2 of the present invention.

In an image matching device 15b and a patient positioning device 16b according to this embodiment, a template setting unit 25 and a template matching unit 26 are added to those represented in Embodiment 1, whose configuration is represented in FIG. 8. According to this configuration, after the matching with a bone (global matching), matching using a template corresponding to an affected part (target cancer) (local matching) can be performed, so that a matching operation and a positioning operation can be performed more precisely than those only by the global matching. Because, regarding a soft tissue other than the head and neck area, especially such as the lungs, liver, and prostate, bones are not present in the proximity thereof, a case might occur that accuracy required for the radiation treatment cannot be satisfied only by the positioning operation with the bone; therefore, in this case, a method is effective in which a template matching operation is performed by setting the neighborhood of the affected part (target cancer) as a template.

In the template setting unit 25, a template image is registered. Using the calculation result by the ICP calculation unit 22 ($\Delta X$, $\Delta Y$, $\Delta Z$, $\Delta A$, $\Delta B$, $\Delta C$), the MPR section group created from the CT image data for the positioning operation (second CT images) using the oblique-section creation parameters (X-$\Delta X$, Y-$\Delta Y$, Z-$\Delta Z$, A-$\Delta A$, B-$\Delta B$, C-$\Delta C$) is assumed to be used. In this step, a characteristic region in which variation of brightness gradation in the MPR section-group converted from the CT images for the positioning operation is relatively large may be selected as a template.

In the template matching unit 26, a template matching operation is executed within a search range in sliced images of the CT image data for the treatment plan (first CT images), a place is obtained where their correlation value reaches highest, and then a conversion-amount compensation value of the second point group data is obtained so as to translate the characteristic region to this place, as a further compensation value for the conversion amount of the second point group data obtained by the ICP calculation unit 22.

In this template matching operation according to this embodiment, a normalized cross correlation method as a robust method against uniform brightness variations is assumed to be used as a method for obtaining the correlation value. However, it is not limited to this method, but a probability-based similarity such as a mutual information amount can also be utilized as a correlation value. Moreover, a robust and high-speed method such as a partial template method (refer to *1) or a hierarchical search method (refer to *2) can also be used for the template matching operation.

*1) Haruhisa Okuda, Manabu Hashimoto, Kazuhiko Simi and Kazunori Sasaki; "Robust Picture Matching Using Optimum Selection of Partial Templates", IEEJ Transactions on Electronics, Information and Systems; Vol. 124, No. 3, p. 629-636 (2004).

*2) Miwako Hirooka, Kazuhiko Sumi, Manabu Hashimoto and Haruhisa Okuda, "Hierarchical distributed template matching", SPIE Machine Vision Applications in Industrial Inspection V, pp. 176-183 (1997).

In order to perform a matching operation more accurately than the one-piece template matching operation, by setting a plurality of templates for a plurality of CT images for the positioning operation (MPR-section group), a multi-layer multi-template matching method for positioning by the plurality of template images can also be applied. Specifically, three characteristic regions included in respective three consecutive sliced images in the MPR section group are registered as template images. The numeral three is an example, and any number may be used as long as it is more than one. It would be convenient that, when a template is set to the central sliced image among the three consecutive images, the other templates are automatically set to the previous and the next sliced images.

Each of the template images for the positioning operation is matched with all the sliced images of the CT image data for the treatment plan (first CT images), and the total sum of the matching scores (correlation values) with respect to the three templates is defined as a new evaluation score. The calculation of the new evaluation score is performed while constraining the positional relationships of the previous and next slices when the multi-layer multi templates are set.

The slice pitch of the CT images for the positioning operation when the multi-layer multi templates are set is assumed to be N, while that for the treatment plan M. A case is represented in FIG. 9 in which the slice pitches of the CT images for the treatment plan and those for the positioning operation are equal (N=M). A value obtained by summing a result of a positioning-template previous score for the previous slice (P1), a result of a positioning-template central score (C2), and a result of a positioning-template next score for the next slice (N3), P1+C2+N3, for example, is to be a new evaluation score at the specified slice.

Similarly, when the slice pitch condition is N=3M, a value obtained by summing scores for every three slices, such as P1+C4+N7, is to be a new evaluation score (refer to FIG. 10). Moreover, when the slice pitch condition is N=5M, a value obtained by summing scores for every five slices, such as P1+C6+N11, is to be a new evaluation score (refer to FIG. 11). In the examples in which the multi-layer multi templates are used as above represented in FIG. 9 through FIG. 11, N is assumed to be larger than M and to be its multiple number.

In the template matching unit 26, sliced images of the CT image data (first CT image data) and a plurality of template images are matched, a place where the new evaluation score (sum of correlation values for every template image) is highest is obtained, and a conversion amount compensation value is obtained for the second point group data so as to translate a plurality of characteristic regions to this place.

In this case, by removing, using the LMedS (least median squares) estimation method being a robust estimation method, results whose positional errors are relatively large among N template-matching results, and thereby local variation influences can also be removed. According to this operation, template information adapted without conflicting the parameter estimation can be effectively used. Setting of N templates in the multi-layer multi template matching operation is not limited to the axial section, but the templates can be set, using the MPR processing, to the sagittal section or the coronal section, or may be set by combining the orthogonal three sections. According to this configuration, more stable results can be expected to be obtained comparing to a case of matching in a single direction.

In the treatment table control parameter calculation unit 24, after the MPR section according to the result obtained by the ICP calculation unit 22 and the section after detailed translation compensation by the template matching operation have been confirmed, output values obtained by detailed-translation compensating, using the conversion amount compensation values obtained by the template matching unit 26, the results of the output values from the ICP calculation unit 22 (total 6DOF consisting of the translation three-axes and the rotation three-axes), are converted into parameters for controlling the axes of the treatment table to be transmitted, whereby the positioning operation can be performed so that the affected part 11 during the treatment is to be placed at the beam irradiation center 12.

Because the image matching device 15b and the patient positioning device 16b according to this embodiment include the point group data resolution conversion unit 19, the point group data region division unit 20, and the point group data noise removal unit 21 as described above, operations and effects similar to those represented in Embodiment 1 are obtained.

Moreover, the MPR processing unit 23 for creating from the second CT image data, using the oblique-section creation parameters based on the conversion amount obtained by the ICP calculation unit 22, the MPR section group which can be compared with the first CT image data, the template setting unit 25 for registering as a template image the characteristic region selected from the MPR section group, and the template matching unit 26 for obtaining, by matching the sliced images of the first CT image data and the template image, the place where the correlation value is highest, and for obtaining the conversion amount compensation value for the second point group data so as to translate the characteristic region to this place are included; therefore, an effect is obtained that, by compensating (positioning) in detail at the position of the affected part after matching with the bone structure, accurate matching can be performed.

Moreover, the template setting unit 25 registers as a plurality of template images a plurality of characteristic regions existing in respective consecutive MPR sections selected from the MPR section group, and the template matching unit 26 obtains, by matching the sliced images of the first CT image data and the plurality of template images, a place where the sum of the correlation values for the respective template images is highest, and obtains a conversion amount compensation value for the second point group data so as to translate the plurality of characteristic regions to this place; therefore, template matching equivalent to a case where three-dimensional volume data is used as the template can be realized by combining a plurality of two-dimensional template matching. Accordingly, an effect is obtained that equivalent accuracy can be realized without spending more time than the three-dimensional template matching.

Moreover, an effect is obtained that, regarding the MPR section group obtained by the MPR processing unit 23, if the matching is performed by combining templates obtained from arbitrary sections at various angles, not only higher-speed processing can be performed than that of the three-dimensional volume matching, but the accuracy thereof can be maintained in the same level as that in the three-dimensional case.

[Explanation of References]

| | |
|---|---|
| 15a, 15b: | Image matching device |
| 16a, 16b: | Patient positioning device |
| 17: | CT image data reading unit |
| 18: | Point group data generation unit |
| 19: | Point group data resolution conversion unit |
| 20: | Point group data region division unit |
| 21: | Point group data noise removal unit |
| 22: | ICP calculation unit |
| 23: | MPR processing unit |
| 24: | Treatment table control parameter calculation unit |
| 25: | Template setting unit |
| 26: | Template matching unit |

What is claimed is:

1. An image matching device comprising:
   a CT image data reading unit for reading first CT image data and second CT image data;
   a point group data generation unit for generating first point group data and second point group data in a three-dimensional space from sliced images of the first CT image data and the second CT image data, respectively;
   a point group data resolution conversion unit for thinning-out at least one of the first point group data and the second point group data so as to extend a point-group-data array pitch; and
   an ICP (iterative closest point) calculation unit for obtaining, using an ICP method, a conversion amount for the second point group data so that an error function of the first point group data and the second point group data outputted from the point group data resolution conversion unit is minimized.

2. An image matching device as recited in claim 1 further comprising
   a region division unit for dividing the first point group data into a plurality of regions, and the second point group data into a plurality of regions corresponding thereto, wherein
   the ICP calculation unit calculates only between each of the regions of the first point group data and each of the corresponding regions of the second point group data.

3. An image matching device as recited in claim 1 further comprising
   a point group data noise removal unit for removing, from at least one of the first point group data and the second point group data, noise data in a portion other than a region where image matching is performed, wherein
   the ICP calculation unit calculates using the first point group data and the second point group data where the noise data has been removed.

4. An image matching device as recited in claim 1 further comprising:
   an MPR processing unit for creating from the second CT image data, using oblique-section creation parameters based on the conversion amount obtained by the ICP calculation unit, an MPR section group which can be compared with the first CT image data;
   a template setting unit for registering as a template image a characteristic region selected from the MPR section group; and
   a template matching unit for obtaining, by matching the sliced images of the first CT image data and the template image, a place where a correlation value is highest, and then obtaining a conversion-amount compensation value for the second point group data so as to translate the characteristic region to this place.

5. An image matching device as recited in claim 4 wherein
   the template setting unit registers as a plurality of template images a plurality of characteristic regions existing in respective consecutive MPR sections selected from the MPR section group, and
   the template matching unit obtains, by matching the sliced images of the first CT image data and the plurality of template images, a place where the sum of correlation values for the respective template images is highest, and a conversion amount compensation value for the second point group data so as to translate the plurality of characteristic regions to this place.

6. A patient positioning device comprising:
   an image matching device including:
   a CT image data reading unit for reading first CT image data and second CT image data;
   a point group data generation unit for generating first point group data and second point group data in a three-dimensional space from sliced images of the first CT image data and the second CT image data, respectively;

a point group data resolution conversion unit for thinning-out at: Least one of the first point group data and the second point group data so as to extend a point-group-data array pitch; and an ICP (iterative closest point) calculation unit for obtaining, using an ICP method, a conversion amount for the second point group data so that an error function of the first point group data and the second point group data outputted from the point group data resolution conversion unit is minimized; and a treatment table control parameter calculation unit for calculating parameters for controlling driving axes of a treatment table according to the conversion amount obtained by the ICP calculation unit.

7. A patient positioning device as recited in claim 6, wherein the image matching device further includes a region division unit for dividing the first point group data into a plurality of regions, and the second point group data into a plurality of regions corresponding thereto, and the ICP calculation unit calculates only between each of the regions of the first point group data and each of the corresponding regions of the second point group data.

8. A patient positioning device as recited in claim 6, wherein the image matching device further includes a point group data noise removal unit for removing, from at least one of the first point group data and the second point group data, noise data in a portion other than a region where image matching is performed, and the ICP calculation unit calculates using the first point group data and the second point group data where the noise data has been removed.

9. A patient positioning device as recited in claim 6, wherein the image matching device further includes:

an MPR processing unit for creating from the second CT image data, using oblique-section creation parameters based on the conversion amount obtained by the ICP calculation unit, an MPR section group which can be compared with the first CT image data;

a template setting unit for registering as a template image a characteristic region selected from the MPR section group; and a template matching unit for obtaining, by matching the sliced images of the first CT image data and the template image, a place where a correlation value is highest, and then obtaining a conversion-amount compensation value for the second point group data so as to translate the characteristic region to this place; and the treatment table control parameter calculation unit calculates the parameters for controlling the driving axes of the treatment table according to the conversion amount obtained by the ICP calculation unit and the conversion amount compensation value obtained by the template matching unit.

10. A patient positioning device as recited in claim 9, wherein the template setting unit registers as a plurality of template images a plurality of characteristic regions existing in respective consecutive MPR sections selected from the MPR section group, and the template matching unit obtains, by matching the sliced images of the first CT image data and the plurality of template images, a place where the sum of correlation values for the respective template images is highest, and a conversion amount compensation value for the second point group data so as to translate the plurality of characteristic regions to this place.

* * * * *